United States Patent [19]

Funatsu

[11] Patent Number: 4,479,629
[45] Date of Patent: Oct. 30, 1984

[54] MOLDING AID FOR CRANIOPLASTY

[76] Inventor: Noboru Funatsu, 15-4, Doyamo-cho, Kita-ku, Osaka-shi, Osaka, Japan

[21] Appl. No.: 462,000

[22] Filed: Jan. 28, 1983

[51] Int. Cl.³ .............................................. B29C 11/00
[52] U.S. Cl. .................................... 249/53 R; 33/176; 33/177; 249/127; 249/157; 249/187 R; 264/222; 264/DIG. 30; 425/2
[58] Field of Search ................. 264/271.1, 279.1, 339, 264/222, DIG. 30; 425/2; 3/1.9, 1.91; 128/92 C; 428/369, 370; 33/177, 176, 175, 483; 249/53 R, 187 R, 157, 127

[56] References Cited

U.S. PATENT DOCUMENTS 2,154,169  4/1939  Koehler ..................... 264/DIG. 30
2,682,725  7/1954  Atwood ..................................... 425/2
2,790,245  4/1957  Wilkes ....................................... 33/177
3,724,083  4/1973  Mehl ......................................... 33/177

FOREIGN PATENT DOCUMENTS 266392  1/1950  Switzerland ............................ 33/177

Primary Examiner—Jay H. Woo
Assistant Examiner—Michael McGurk
Attorney, Agent, or Firm—Armstrong, Nikaido, Marmelstein & Kubovcik

[57] ABSTRACT

An aid for molding a filling material used in the cranioplasty to fill in a defective part of the skull. The aid allows a quick, efficient molding. It includes a bar made of an elastic material and being of a substantially L-shape section and a core member embedded therein to maintain the aid in a desired position.

3 Claims, 8 Drawing Figures

MOLDING AID FOR CRANIOPLASTY

The present invention relates to a molding aid for molding a filling material used in cranioplasty to fill in a defective part of the skull.

The filling material used in the cranioplasty includes three types, namely, osseous materials, metallic materials and synthetic resins. Osseous materials have a merit of having a large possibility of physiological accretion taking place once united with the skull, but have a number of demerits: necessity of reoperation by the use of artificial bone when melting took place after the plastic operation, and difficulty in preservation and sterilization. Metallic materials have demerits of not transmitting an X-ray, high thermal conductivity, poor flexibility to a secondary lesion, difficulty in shaping, liablity to damage the surrounding soft tissues, and high cost. Synthetic resins have come lately to be widely used as defect-filling materials as a result of advancement in the application technology.

For this purpose, synthetic resins of a quick setting type are used. They are accepted as excellent materials, because they are moldable in any desired shape and meet the requirements for a filling material, namely, less harm to bio-tissue, ease of manufacture, sterilization, use in operation, procurement and preservation, proper rigidity and specific gravity for protection of the contents of the skull, less incompatibility to the body, and no interference to examinations using X-ray or electro-magnetic waves.

The cranioplastic method with a rapid-setting resin is divided into two types: in one, first filling the defective part in the skull with wet cotton, gauze or the like to simulate the curved surface of the normal skull and then placing a sterilized polyethylene film thereon, or placing the film directly over the defective part in the skull, and pouring a liquid resin on the film, and allowing it to set; in the other, making a plaster mold using the patient's bone as pattern and pouring a liquid resin to set therein. The former method, in which a resin is poured onto a polyethylene film laid directly or indirectly on the brain tissues and allowed to set, is accompanied by some risk of the brain tissues being subjected to various stimulations. Moreover, it is not so easy to adjust the resulting artificial bone to a desired thickness. The latter method using a plaster mold is highly complicated and time-consuming and is accompanied by the risk of the patient's bone being broken or melted. This makes it impossible to prepare the desired mold.

An object of the present invention is to provide a molding aid which permits the molding of a filling material in the cranioplastic operation in a quick, efficient manner, allowing adjustment of the shape and thickness of the resulting artificial bone.

Other objects and features of the present invention will become apparent from the following description taken with reference to the accompanying drawings, in which.

Figure 4:
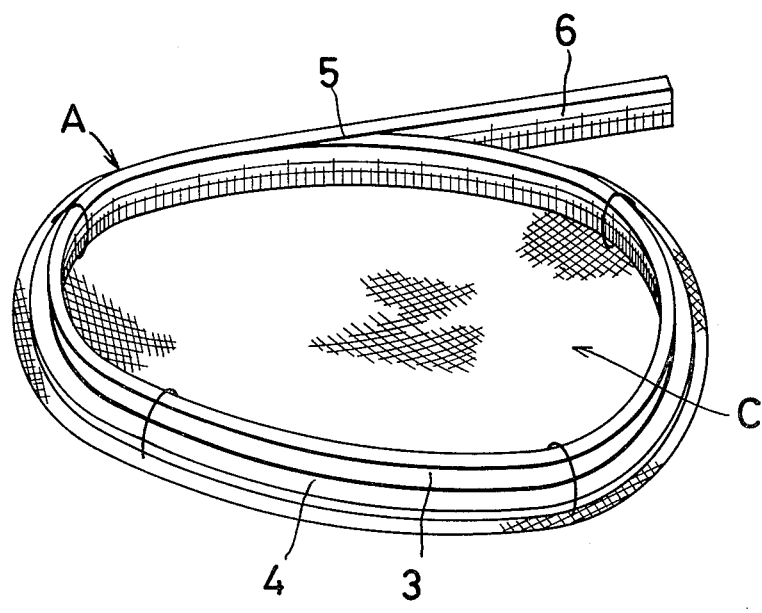

FIGS. 3(a)–3(e) are perspective views showing sections of other embodiments; and FIG. 4 is a perspective view showing how the molding aid is used in a cranioplastic operation.

Figure 1:
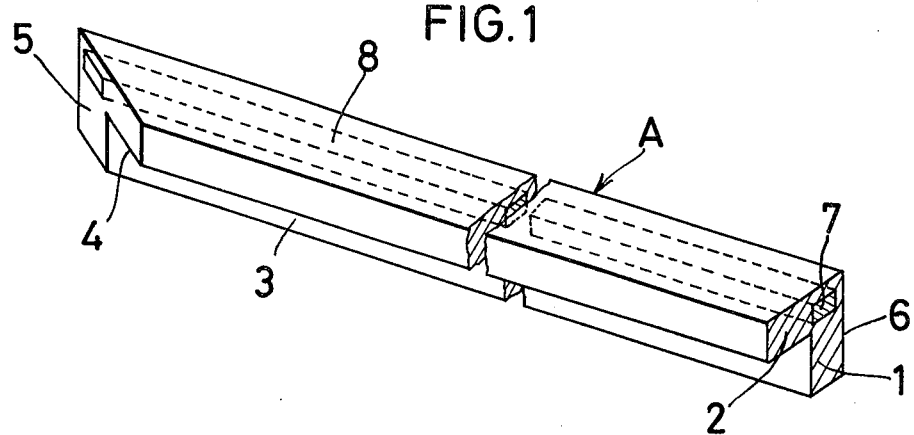
FIG. 1 is a perspective view of a molding aid embodying the present invention.

Shown in FIG. 1 is an embodiment of a molding aid for cranioplastic material according to this invention. This molding aid A is of a substantially L-shape section with a vertical side 1 and a horizontal side 2. The width of their vertical and horizontal sides may be equal to each other or different. However, the angle between the inside surface 3 of the vertical side 1 and that 4 of the horizontal side should be a right angle or close thereto. Its sectional shape may be as illustrated in FIGS. 3(a)–3(e). The reason therefor is that it is convenient for enabling the aid to fit closely and stably to the rim of a defective part in the skull.

At least one of the end faces 5 of the molding aid should be at an acute angle to the inside surface 3 of its vertical side and perpendicular to the inside surface 4 of its horizontal side. The reason for making the end face 5 at an acute angle to the inside surface of the vertical side 3 is to make its continuance to the outside surface 6 of the vertical side as smooth as possible when, as shown in FIG. 4, the end face 5 is brought into contact with the outside surface 6 of the vertical side so as to make the molding aid into a loop (with the outside surface 6 of the vertical side forming the inside surface of the loop). The above-mentioned acute angle should be as small as possible for greater smoothness at the connection of the loop but since, if it is too small, the resulting sharp edge might accidentally injure the brain tissues or other adjoining areas when the aid is used for molding the defective part in the skull, it is advisable to make it 30°–60° and have the edge properly rounded.

The molding aid A of the present invention should be made of an elastometric material such as natural rubber, synthetic rubber or a synthetic resin. Since this is intended for use in surgical operations, the material is naturally required to be safe from dissolution, elution, etc. and hygienic, and contain no harmful additive. When it is to be used repeatedly, not as a disposable article, it is also required to be sterilizable. Hence, e.g. silicone resin is one of the preferred materials.

A flexible core 7 is embedded in the body of such a rubbery material to allow the molding aid A to be readily bendable and straightenable and to keep it bent. The underlying principle is the same as with the conventional flexible rule. In view of the intended use, the flexible core 7 should be made of a material harmless to the human body. A wire of gold, silver, annealed steel, or aluminum is good for this purpose. Surface treatment or elaborate encapsulating with a rubbery material is required to avoid dissolving-out of harmful metallic ions if copper, lead or their alloys are used. Encapsulating the core 7 in the rubbery material may be done either by forming a longitudinal cavity in a body of rubbery material in advance, inserting the core 7 in the cavity and then closing it at both ends, or, by molding the rubbery material in a predetermined shape, with the core 7 embedded in it completely, so that no part is exposed. The core 7 may be of a square or round section. This has nothing to do with the effect of the present invention.

Figure 2:
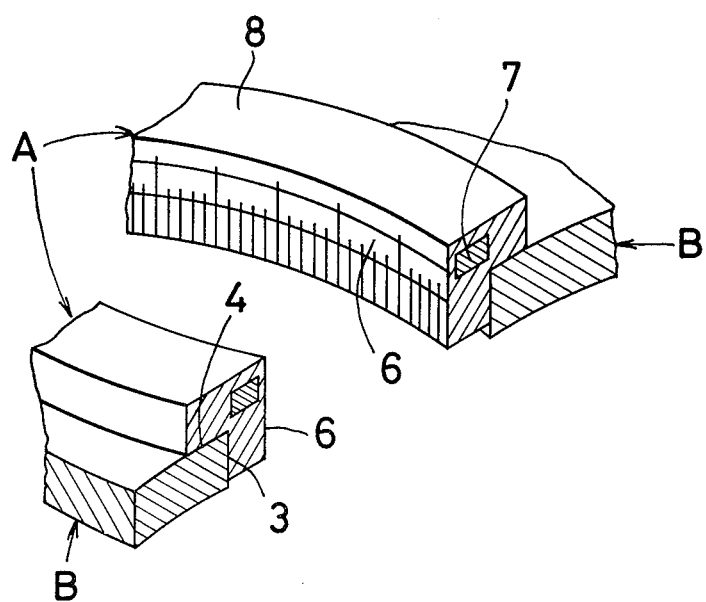
FIG. 2 is a partially sectional perspective view showing how the molding aid is applied to the rim of a defective part of the skull.
Figure 3A:
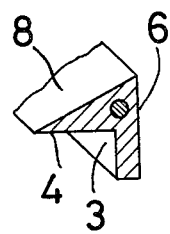
Figure 3C:
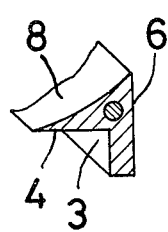
Figure 3B:
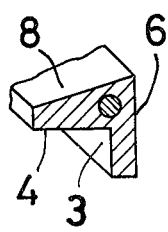
Figure 3D:
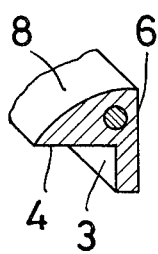
Figure 3E:

The molding aid A of the present invention is used to model the shape of a defective part in the skull with the inside surface 3 of its vertical side and the inside surface 4 of its horizontal side in contact with the rim of the defective part in the skull B in the manner as illustrated in FIG. 2. Hence, the width of the inside surface 3 of its vertical side 1 should be less than the thickness of the skull B. If the vertical side 1 is too long, it could press on the brain tissues, damaging them.

The width of the inside surface 4 of the horizontal side is sufficient to attach it onto the edge of the defective skull. The finished piece of artificial bone should fit closely in the bone aperture (defective part in the skull), but a slight gap is practically acceptable. Therefore, its thickness may be approx. 2-3 mm so that the inside surface 3 of the vertical side can hang down from the rim of the defective skull and so that the molding aid A will not come away from the bone aperture or be bent during the molding. The inside surface 3 of the vertical side is parallel to its outside surface 6 while the inside surface 4 and the outside surface 8 of the horizontal side may be parallel to each other as shown in FIGS. 1 and 2 or not parallel as shown in FIG. 3 but inclined or curved with respect to its inside surface. Although it is necessary to predetermine the dimensions of the molding aid for an adult or a child or according to the position of the defective part, as a rough guide, the width of the outside surface 6 of the vertical side and that of the outside surface 8 of the horizontal side may be 3-10 mm or so and the overall length of the molding aid be approx. 40 cm to ensure its close fitting to the rim of the defective part and the dependability of the molding with it.

In using the molding aid of the present invention in cranioplastic operation, first the curved surface in the defective part in the skull is formed on a wire mesh C with fingers to properly reproduce the original configuration with irregularities presumed from that of the surrounding areas. Any wire mesh can be used, but a stainless steel wire with a mesh of about 1-3 mm is preferable. Then the wire mesh on which the imaginary surface of the defective part in the skull has been copied is placed with its concave side up as shown in FIG. 4, a sterilized sheet of polyethylene film (not shown) is laid on it. The molding aid A which has been looped to simulate the defective part in the skull is placed inverted with the outside surface 8 of its horizontal side in contact with the polyethylene film on the wire mesh C and the molding aid is tied to the wire mesh C at several points using thread or similar material.

To maintain the shape of the molding aid from when it is used to simulate the defective part in the skull until it is placed on the wire mesh, one or both of the outside surface 6 of the vertical side and the outside surface 8 of the horizontal side should be graduated so that one end of the molding aid A can be brought back to the right position even if it should be somewhat displaced in the course of the abovementioned procedure. When the wire mesh C and the molding aid A have been fixed together, the liquid resin is poured on the polyethylene film.

As the liquid resin, methacrylic rapid-setting resin (Codman Co. in U.S.A., called Cranioplastic kit) may be used. This resin sets in approx. 15 minutes after pouring. Before its setting is complete, the thickness of the resin layer is adjusted according to the original thickness of the bone. At the same time, tiny holes are formed as necessary (for drainage after the plastic operation and/or for the fixing and reinforcement of the molded part through ingress of the granulation tissue). For facilitating adjustment of the thickness of the poured resin layer, it is preferable to put a height-indicating graduation on the outside surface 6 of the vertical side. This graduation may consist of one or more parallel, longitudinal lines or may be adapted for color indentification by laminating layers of different colors to form the body of rubbery material.

After the poured resin has set, the molding aid A and the wire mesh C are removed. Since the molding aid of the present invention is placed on the wire mesh with the concave side up and the resin is poured to set therein, the resulting artificial bone will be of a trapezoidal section. This is advantageous in that its accidental dropping into the skull interior during the operation is prevented. In accordance with the present invention, the molding of cranioplastic material is possible in the course of a cranioplastic operation with a fine result.

What is claimed is:

1. A molding aid for molding a filling material used in cranioplasty, comprising a body in the shape of a bar made of an elastomeric material and being of a substantially L-shaped cross section and having a vertical side, a horizontal side, and a core member embeddded in said body along the axis thereof and wherein said core member is made of a flexible material whereby the material selected is such that the said molding aid will be readily bendable and straightenable, and at least one of the end surfaces of the molding aid being at an acute angle with respect to the inner surface of said vertical side and being perpendicular to th einner surface of said horizontal side.

2. The molding aid as claimed in claim 1, wherein at least one of the outer surfaces of said vertical and horizontal sides is provided with a graduation extending in the axial direction.

3. The molding aid as claimed in claim 1, wherein the outer surface of said vertical side is provided with a graduation for indicating the height.

* * * * *